US008498870B2

(12) United States Patent
Brandt (10) Patent No.: US 8,498,870 B2
(45) Date of Patent: Jul. 30, 2013

(54) MEDICAL ONTOLOGY BASED DATA AND VOICE COMMAND PROCESSING SYSTEM

(75) Inventor: Samuel I. Brandt, Malvern, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1166 days.

(21) Appl. No.: 12/358,301

(22) Filed: Jan. 23, 2009

(65) Prior Publication Data
US 2009/0192800 A1 Jul. 30, 2009

Related U.S. Application Data

(60) Provisional application No. 61/023,200, filed on Jan. 24, 2008.

(51) Int. Cl.
*G10L 21/00* (2006.01)
(52) U.S. Cl.
USPC ........................................................ 704/270.1
(58) Field of Classification Search
USPC ........................................................ 704/270.1
See application file for complete search history.

(56) References Cited

U.S. PATENT DOCUMENTS

| 6,785,654 | B2 | 8/2004 | Cyr et al. |
| 6,999,930 | B1 * | 2/2006 | Roberts et al. ............. 704/270.1 |
| 7,146,321 | B2 | 12/2006 | Cyr et al. |
| 7,369,998 | B2 | 5/2008 | Sarich et al. |
| 7,426,468 | B2 | 9/2008 | Coifman et al. |
| 7,734,471 | B2 * | 6/2010 | Paek et al. .................. 704/270.1 |
| 2002/0143533 | A1 | 10/2002 | Lucas et al. |
| 2004/0083092 | A1 * | 4/2004 | Valles ................................ 704/9 |
| 2004/0102971 | A1 | 5/2004 | Lipscher et al. |
| 2006/0020444 | A1 * | 1/2006 | Cousineau et al. ............... 704/1 |
| 2006/0020466 | A1 * | 1/2006 | Cousineau et al. ........... 704/257 |
| 2006/0020492 | A1 * | 1/2006 | Cousineau et al. ............. 705/2 |
| 2006/0053035 | A1 * | 3/2006 | Eisenberg ........................ 705/2 |
| 2006/0059028 | A1 * | 3/2006 | Eder ................................. 705/7 |
| 2006/0173635 | A1 * | 8/2006 | Yakhini et al. ................. 702/20 |
| 2006/0190836 | A1 | 8/2006 | Ling Su et al. |
| 2006/0292302 | A1 * | 12/2006 | Chodelka et al. .......... 427/248.1 |
| 2007/0016450 | A1 * | 1/2007 | Bhora et al. ...................... 705/3 |
| 2007/0038449 | A1 | 2/2007 | Coifman |
| 2007/0156403 | A1 | 7/2007 | Coifman |
| 2009/0018867 | A1 | 1/2009 | Reiner |

* cited by examiner

*Primary Examiner* — Michael N Opsasnick
(74) *Attorney, Agent, or Firm* — Joshua Ryan (57) ABSTRACT

A computerized integrated order entry and clinical documentation and voice recognition system enables voice responsive user entry of orders. The system includes a voice recognition unit for detecting spoken words and converting detected spoken words to data representing commands. A data processor, coupled to the voice recognition unit, processes the data representing commands provided by the voice recognition unit, to provide order and documentation related data and menu options for use by a user, by interpreting the data representing commands using an ordering and documentation application specific ontology and excluding use of other non-ordering or non-documentation application specific ontologies. The ordering application enables initiating an order for medication to be administered to a particular patient, or additional ordered services to be performed. A user interface processor, coupled to the data processor, provides data representing a display image. The display image, includes the order related data and menu options provided by the data processor and supports a user in selecting an order for medication to be administered to a particular patient.

22 Claims, 8 Drawing Sheets

| 20 Vowel Phonemes for American English AKSES Character /Phoneme Name/ ||||
|---|---|---|---|
| a, A  /a/ | ā, Ā  /ae/ | aw, AW  /aw/ | ar, AR  /ar/ |
| at, sat, man | ape, pail, tame | awful, bawl, law | art, farm, mar |
| e, E  /e/ | ē, Ē  /ee/ | ow, OW  /ow/ | er, ER  /er/ |
| end, pet, fell | eel, mean, city | out, cow, down | her, fur, skirt |
| i, I  /i/ | ī, Ī  /ie/ | oy, OY  /oy/ | or, OR  /or/ |
| it, wish, rib | eye, sigh, time | oil, boy, loyal | or, tore, floor |
| o, O  /o/ | ō, Ō  /oe/ | oo, OO  /oo/ | air, AIR  /air/ |
| hot, odd, alms | so, low, hope | ooze, zoo, zulu | fair, care, there |
| u, U  /u/ | ū, Ū  /ue/ | uu, UU  /uu/ | ear, EAR  /ear/ |
| up, ago, but | use, few, cute | hook, put, wood | fear, deer, pier |
| AKSES vowel names are not the names of the letters, but are the spoken vowel sound in the key words spelled on the line below. ||||

| 24 Consonant Phonemes for American English AKSES Character /Phoneme Name/ ||||
|---|---|---|---|
| b, B  /b(u)/ | k, K  /k/ | s, S  /s/ | ch, CH  /ch/ |
| bet, tab, lobby | can, lick, picker | sap, pass, fist | chin, church, itch |
| d, D  /d(u)/ | l, L  /l/ | t, T  /t/ | ng, NG  /ng/ |
| dill, lid, older | let, tilt, pullet | ton, pit, metal | wing, tank, going |
| f, F  /f/ | m, M  /m/ | v, V  /v/ | sh, SH  /sh/ |
| fun, muff, iffy | me, rum, timer | van, love, cover | she, push, worship |
| g, G  /g(u)/ | n, N  /n/ | w, W  /w/ | th, TH  /th/ |
| get, tag, piggy | no, tan, funny | win, swim, wash | thin, with, earthy |
| h, H  /h(u)/ | p, P  /p(U)/ | y, Y  /y/ | t̄h, T̄H  /t̄h/ |
| hit, how, where | pin, nap, happy | yet, young, yip | this, bother, seethe |
| j, J  /j(u)/ | r, R  /r/ | z, Z  /z/ | zh, ZH  /zh/ |
| jet, gel, budget | run, nor, pert | zoo, ooze, fuzzy | azure, measure |
| Names of AKSES consonants are not the letter name, but the isolated speech sound, followed, where necessary, by the softest possible schwa. ||||

| Action | DRUG | FORM | DOSE | ROUTE | FREQUENCY | TIMING | DURATION | PRIORITY | REASON |
|---|---|---|---|---|---|---|---|---|---|
| ☑ ... | (BUMEX ORAL) BUMETANIDE | TABLET | 2 mg | TAKE ORALLY | 2 TIMES PER DAY | ... | ... | ... | ... |

Popup (605):
- BUMETANIDE TABLET 3 mg TAKE ORALLY 1 TIME PER DAY
- BUMETANIDE TABLET TAKE ORALLY
- ...
- 2 TIMES PER DAY
- 4 TIMES PER DAY
- 1 TIME PER DAY
- 3 TIMES PER DAY
- 1 TIME EVERY 8 HOURS
- 1 TIME EVERY 12 HOURS
- 1 TIME EVERY 2 DAYS
- 1 TIME EVERY 6 HOURS
- 5 TIMES EVERY 1 WEEK
- ENTER TEXT HERE

MEDICAL ONTOLOGY BASED DATA AND VOICE COMMAND PROCESSING SYSTEM

This is a non-provisional application of provisional application Ser. No. 61/023,200 filed Jan. 24, 2008, by S. I. Brandt.

FIELD OF THE INVENTION

This invention concerns integrating computerized clinical documentation and order entry with voice recognition, enabling voice responsive completion of clinical documentation and user entry of orders based upon an application specific ontology. For example, when dictating about the physical exam of the heart, the speech recognition is constrained to a language model based upon the segment of the documentation knowledge ontology which concerns the heart exam. As the speaker traverses sections of the document, the corresponding section of the ontology is synchronized so that recognition is contextually sensitive.

BACKGROUND OF THE INVENTION

Continuous speech recognition is useful for converting the spoken word into the written word. However, known continuous speech recognition systems provide an output comprised of unstructured text. Such known continuous speech recognition systems are therefore of limited use for providing point of care decision support or aggregate outcomes analysis.

Alternatively, hierarchical lists of clinical concepts and values can be used to provide point and click user interfaces for clinical documentation. These user interfaces tend to be slow, require numerous user clicks and are therefore limited in their application. A system according to invention principles addresses these deficiencies and related problems.

SUMMARY OF THE INVENTION

A system improves the accuracy of continuous speech recognition in clinical applications and generates structured medical documentation using both speech to free text conversion and hierarchical clinical documentation templates. A computerized integrated order entry and voice recognition system enables voice responsive user entry of orders. The system includes a voice recognition unit for detecting spoken words and converting detected spoken words to data representing commands. A data processor, coupled to the voice recognition unit, processes the data representing commands provided by the voice recognition unit, to provide order related data and menu options for use by a user, by interpreting the data representing commands using an ordering application specific ontology and excluding use of other non-ordering application specific ontologies. The ordering application enables initiating an order for medication to be administered to a particular patient. A user interface processor, coupled to the data processor, provides data representing a display image. The display image, includes the order related data and menu options provided by the data processor and supports a user in selecting an order for medication to be administered to a particular patient.

BRIEF DESCRIPTION OF THE DRAWING

FIG. 3 illustrates an example of phoneme types.

DETAILED DESCRIPTION OF THE INVENTION

A system improves the accuracy of continuous speech recognition within clinical applications and generates fully structured medical documentation and order entry by both speech to free text conversion and by using hierarchical clinical documentation and order templates. The system provides continuous speech recognition enabling voice responsive navigation and selection of spoken terms from structured hierarchical clinical documentation and order ontologies in a reduced target term recognition space advantageously improving probability of selection of a correct word or term match. The system further provides structured clinical documentation and ordering supporting clinical decision making by a physician and both enhances continuous speech recognition and improves its suitability in the clinical domain. The system enables continuous speech recognition to generate structured documentation which is programmatically understandable, and suitable for point of care decision support and aggregate outcomes analysis.

An ontology as used herein comprises a data model that represents a set of concepts within a domain and the relationships between those concepts and is used to reason about the objects within that domain. Specifically, the data model may comprise a dictionary or vocabulary comprising a set of codes, terms, identifiers and words used for a particular clinical application or function. An ordering application specific ontology comprises an ordering application specific vocabulary (e.g., a vocabulary of concepts and concept relationships). Further, order related data comprises order related parameters identifying at least one of, (a) quantity, (b) a route of administration of a medical treatment, (c) a frequency of administering a treatment, (d) a form of medical treatment, (e) timing of a laboratory test, (f) settings for a ventilator and (g) type of bed for admission.

A template as used herein comprises a form or displayed arrangement of cells or data fields for presenting data items. A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure. Workflow comprises a sequence of tasks performed by a device or worker or both. A document or record comprises a compilation of data in electronic form and is the equivalent of a paper document and may comprise a single, self-contained unit of information. A document or record comprises a compilation of data in electronic form and is the equivalent of a paper document and may comprise a single, self-contained unit of information.

Figure 1:
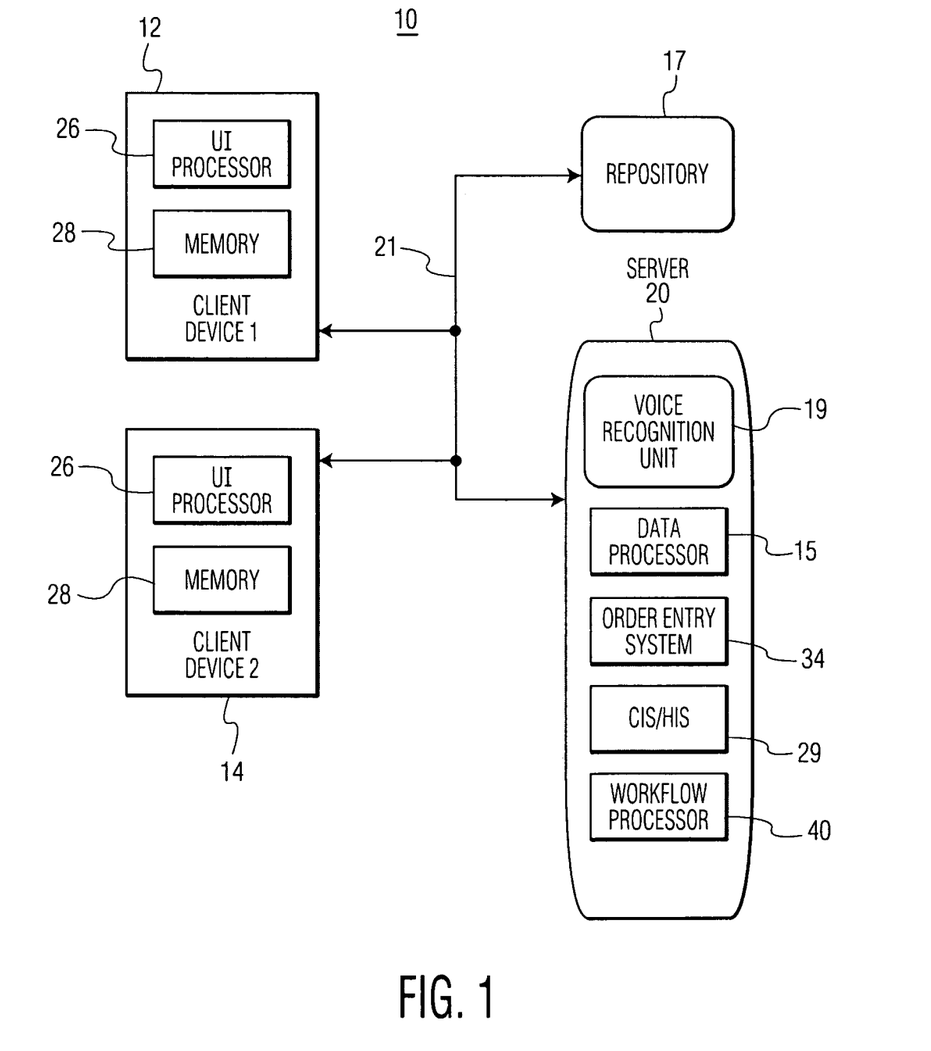
FIG. 1 shows a computerized integrated order entry and voice recognition system enabling voice responsive user entry of orders, according to invention principles.

FIG. 1 shows a computerized integrated order entry and voice recognition system enabling voice responsive user entry of orders. System 10 includes client devices (workstations) 12 and 14, repository 17 and server 20. The system 10 devices are interconnected and bidirectionally communicate via network 21 such as a LAN (Local Area Network) or other type of network. A client device (workstation) 12 or 14 includes user interface processor 26 and memory unit 28 and may comprise a personal computer, notebook, PDA or phone, for example. Repository 17 (comprising one or more local or remote databases) includes information comprising an ordering application specific ontology and a clinical documentation specific ontology as well as multiple template candidate order sets. The template candidate order sets individually include multiple candidate items for order and associated corresponding related order parameters and information in repository 17 associates an individual item for order with multiple related order parameters. Repository 17 also includes electronic patient medical records, data representing recommended guidelines for treating different medical conditions, individual treatment order templates, medical documentation templates, treatment orders placed by physicians for patients and patient treatment plans and documentation indicating compliance with recommended treatment guidelines, for example. Server 20 comprising one or more servers or computers, includes voice recognition unit 19, data processor 15, order entry system 34 and Clinical Information System (CIS) and Hospital Information System (HIS) 29 and workflow processor 40.

Voice recognition unit 19 detects spoken words and converts detected spoken words to data representing commands. Data processor 15, coupled to voice recognition unit 19, processes the data representing commands provided by voice recognition unit 19, to provide order related data and menu options for use by a user, by interpreting the data representing commands using an ordering application specific ontology and excludes use of other non-ordering application specific ontologies. The ordering application specific ontology comprises an ordering application specific vocabulary including ordering specific, codes, terms and identifiers. The ordering application provided by order entry system 34 enables a user to initiate an order for medication to be administered to a particular patient. User interface processor 26, coupled to data processor 15, provides data representing a display image. The display image includes the order related data and menu options provided by data processor 15 and supports a user in selecting an order for medication to be administered to a particular patient. Order entry system 34 supports user ordering of treatment to be administered to a patient via one or more display images provided by user interface processor 26 on workstation 12 or 14.

In a further embodiment, FIG. 1 also comprises a clinical documentation and voice recognition system enabling voice responsive user completion of clinical documentation. In this embodiment, data processor 15 processes the data representing commands provided by voice recognition unit 19, to provide clinical documentation related text data and menu options for use by a user, by interpreting the data representing commands using a clinical documentation application specific ontology and excluding use of other non-clinical documentation application specific ontologies. The clinical documentation application enables user data entry documenting clinical activities performed for a particular patient. User interface processor 26 provides data representing a display image including the clinical documentation related data and menu options provided by data processor 15 and supports a user in data entry documenting clinical activities performed for a particular patient. Clinical Information System (CIS) and Hospital Information System (HIS) 29 presents forms to users via workstation 12 or 14 enabling a user to enter documentation for the patient indicating data identifying which tests were ordered, the medical condition of the patient and reasons for ordering medications or not ordering medications, for example. Workflow task processor 40 prompts a user (e.g., healthcare worker) with order related tasks and to complete documentation, indicating an action taken by the healthcare worker in treating the patient, and documenting compliance with the recommended guidelines.

Workflow comprises a sequence of tasks performed by a device or worker or both. A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams.

Known voice recognition systems perform continuous speech recognition by capturing phonemes as representations of syllables of speech and mapping a small series of phonemes into word phrases using a vocabulary model. By determining the highest probability match of a series of phonemes to a phrase and repeating the matching process for each sequential series of phonemes known systems convert speech into written words. The phrases consist of word groups which are associated with each other typically simply as a reflection of frequency of use. As such, generated text consists of a series of words which match a vocabulary model, but which are not constrained to, or mapped to, a hierarchical structured documentation ontology model. Also, because there is no constraint imposed upon the speech to be recognized, phonemes can be associated with phrases which are contextually unrelated to entities, e.g., clinical entities, being described. For example, during dictation concerning a heart examination, a description of a soft blowing murmur could be interpreted as a "soft bowing femur" since there is no guidance to know what kinds of things could or should be said in the context of dictating results of a heart examination.

Figure 2:
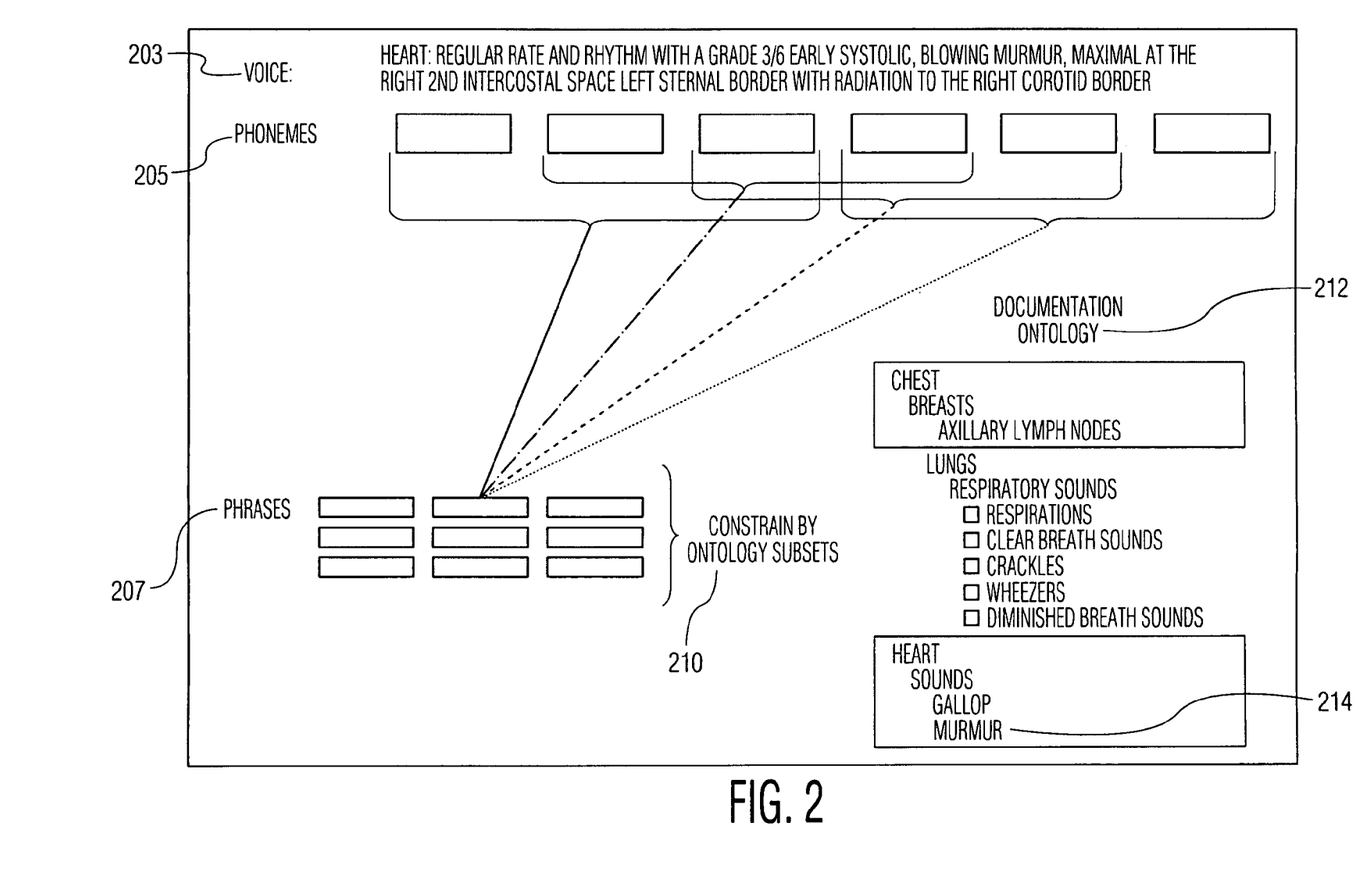
FIG. 2 illustrates system operation involving capturing phonemes as representations of syllables of speech and mapping phonemes into a vocabulary model consisting of word phrases, according to invention principles.

FIG. 2 illustrates capturing phonemes as representations of syllables of speech and mapping phonemes into a vocabulary model consisting of word phrases performed by data processor 15 (FIG. 1). A physician performing an audiological examination of a patient heart dictates a heart examination phrase 203 "heart: regular rate and rhythm with a grade 3/6 early systolic, blowing murmur, maximal at the right $2^{nd}$ intercostal space left sternal border with radiation to the right carotid artery". Voice recognition unit 19 converts detected spoken words of phrase 203 to data representing commands in the form of phonemes 205. FIG. 3 illustrates an example of phoneme types. Voice recognition unit 19 captures spoken phrase 203 in the form of data (sound wave representation) files and uses mapping information in repository 17 to associate the wave files with a string of phonemes 205 as known. The string of phonemes 205 are further matched to text phrase 207 by data processor 15.

Figure 4:
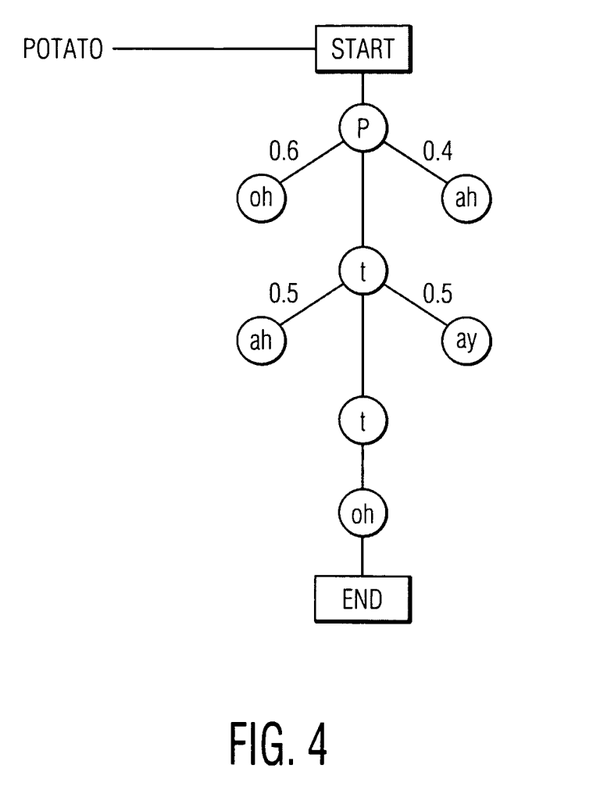
FIG. 4 illustrates operation of known speech recognition systems.

FIG. 4 illustrates operation of known voice recognition matching of a string of phonemes to a text phrase, based upon probability. FIG. 4 illustrates a known Markov probabilistic model for converting phonemes to text phrases within a three syllable word POTATO. Such a system may limit phrase matching space using a Lexical tree or Lookahead model, for example. Within a speech recognition model (such as the one for Potato above), a system constrains the corpus of potential associations to those that are further down the tree from the current point. Another Language Model, the Lookahead model, limits phonetic phrase matches to those that fit a language of expressible phrases.

Data processor 15 (FIG. 1) advantageously places an additional set of constraints on the interpretation of the set of phonemes 205 (FIG. 2) to provide text phrase 207, both by limiting the recognizable expressible phrases to a subset 210 of those that are found within an external ontology, such as one for placing orders or documenting clinical notes, and also by imposing a lexical tree 212, based upon a current navigational position within an external ontology. The current navigational position may be associated with ordering dopamine in an order entry application and image display presented on client device 12, or documenting a sound, here heart murmur 214 within the navigational tree 212 having corresponding display images presented on client device 12, for example. Thereby, of all of the words in medical English, only those that fit within the external ontology, within the current lexical tree associated within a current navigational position in a navigational hierarchy, are considered for probabilistic matching. Data processor 15 interprets the data representing commands (phonemes) using an ordering application or clinical documentation specific ontology and excludes use of other non-ordering or non documentation application specific ontologies. The ordering or documentation application enables initiating an order for medication to be administered to a particular patient or enables user data entry documenting clinical activities performed for a particular patient.

Data processor 15 adaptively, dynamically limits an ordering application specific ontology comprising recognizable expressible phrases to a subset of phrases associated with a current navigational position within an ordering application. Data processor 15 adaptively, dynamically limits a clinical documentation application specific ontology comprising recognizable expressible phrases to a subset of phrases associated with a current navigational position within a clinical documentation application. In structured documentation, a description of the heart includes a subclass of heart sounds, which in turn may include a subset for murmurs, which includes characteristics such as quality, tonality, intensity and timing. In an example, selecting a quality of blowing, and intensity of soft as attributes of a murmur, precisely and unambiguously describes the murmur. Data processor 15 advantageously uses phoneme recognition and a hierarchical term tree structure within a documentation ontology to limit a recognition space for dictation of the result of a heart examination so that term recognition is constrained to those items found within a local area of a documentation ontology. As such, blowing is found to describe quality of a murmur, and soft is found to describe intensity of a murmur, but bowing would be out of context and therefore not recognized.

The system advantageously provides higher accuracy speech recognition since there are fewer similar sounding phrases to confuse a recognition and interpretation process. Also, system interpretation is accelerated since there is a smaller search space. Additionally, system speech recognition substitutes for pointing and clicking or navigating with a mouse in performing clinical documentation using hierarchical navigational documentation lists, and therefore generates structured documentation more easily and quickly than using a mouse or pen interface.

A clinician desiring to document clinical findings selects an appropriate documentation template or starting menu that retrieves data representing a hierarchical navigational structure from an ontology. In an example, a physician documenting a physical examination including cardiac findings, navigates from section to section of a documentation template such as from lung examination to heart examination. Data processor 15 operating in conjunction with voice recognition unit 19, migrates a recognition (interpretation) space to conform to the section currently selected within the documentation template. Words spoken while the lung section is being processed adaptively initiate search by data processor 15 for items within the lung section of the ontology, while words spoken while the heart examination documentation is in process initiates search within the heart section of the ontology. Data processor 15 advantageously associates the speech recognition space to a structured documentation model structure and increases speech recognition accuracy and speed, and provides structured text output.

The system advantageously obviates a need to create lists or trees, and to constrain recognition space to items that are existing within populated elements of the lists or trees. Such lists require substantially complete population of elements involving potentially thousands of items concerning a heart, and putting these into a tree is time-consuming and burdens a user interface and occupies memory. In contrast system 10 recognizes that the target of intended speech lies within a heart section of the ontology, for example and therefore what is said is interpreted by searching for matching text phrases within the heart section of the ontology. It places no limitations on the size of that space or the number of phrases which could be expressed regarding the heart. The system advantageously constrains its recognition space to a neighborhood within one or more ontologies and is applicable for use with structured documentation in any field in which documentation is post-processed, indexed, or subject to rules including the legal profession, research, and academic fields. The system uses an ontology for structured clinical documentation, coupled with speech recognition, to provide a continuous speech interface for documentation using the ontology.

Figure 5:
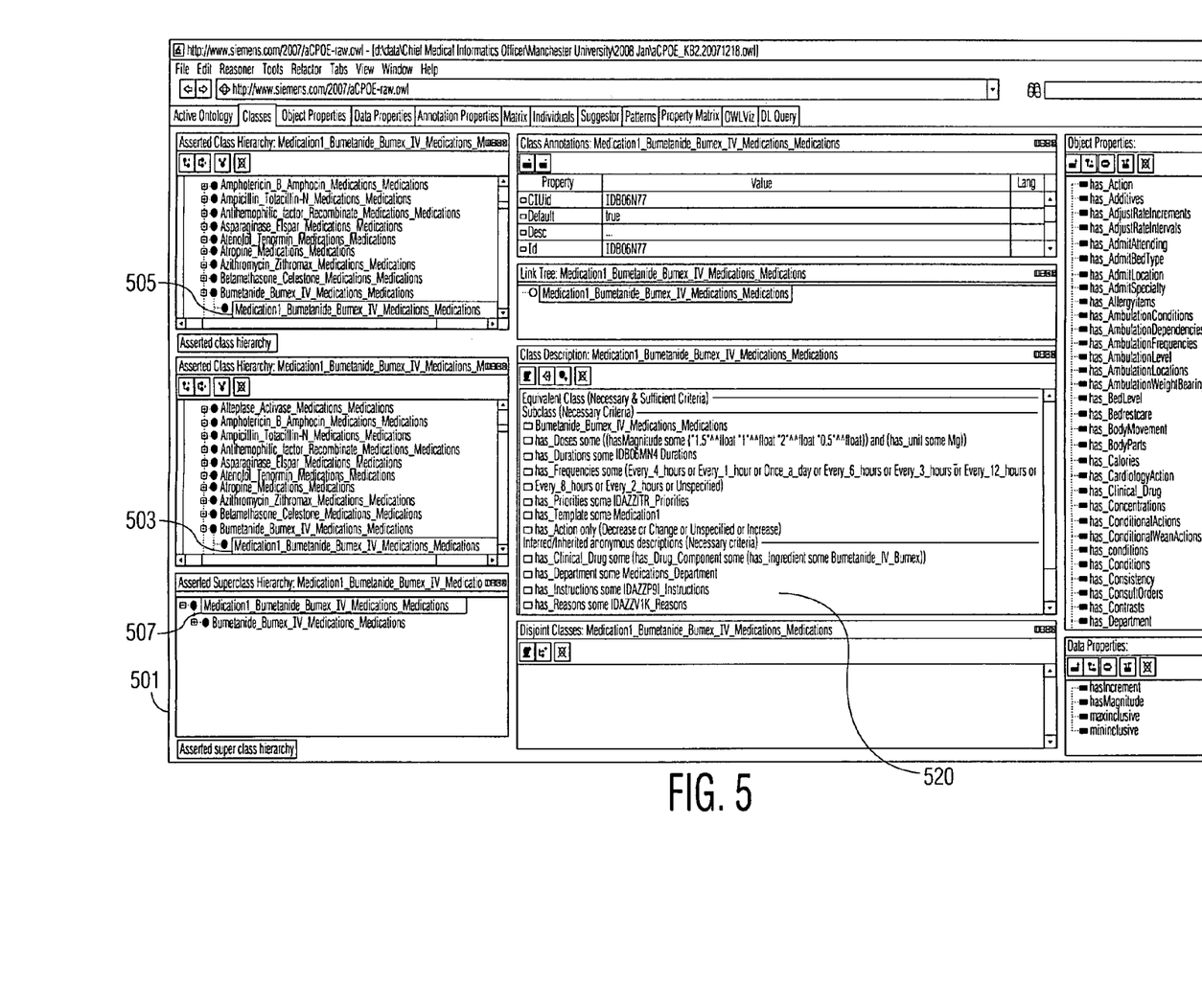
FIG. 5 shows a display menu used by a computerized integrated order entry and voice recognition system employing an ordering ontology, according to invention principles.

FIG. 5 shows display menu 501 used by computerized integrated order entry and voice recognition system 10 employing an ordering ontology. Data processor 15 (FIG. 1) processes phoneme data representing a command (a spoken phrase mentioning Bumex) to select a particular medication (here Bumex) provided by voice recognition unit 19, to provide order related data and menu options supporting ordering Bumex for use by a user. Specifically, in response to a user spoken phrase mentioning Bumex, data processor 15 initiates navigation to Bumex representative data items 503, 505 and 507 presenting drug hierarchies in image windows in user interface image window 501 and presents Bumex specific ordering related properties in window 520 and associated Bumex property relationships. The ordering application uses an ontology to manage display menu navigation so that if a user wants to place an order, and selects Bumex, the user view is localized to the portion of the ontology that contains the Bumex order related information and can interrogate the ontology for its related data. Data processor 15 interprets the data representing commands using an ordering application specific ontology and excludes use of other non-ordering application specific ontologies. The ordering application enables initiating an order for medication (Bumex) to be administered to a particular patient.

Data processor 15 interprets the data representing commands by further adaptively, dynamically limiting the ordering application specific ontology comprising recognizable expressible phrases to a subset of phrases associated with a current navigational position within an ordering application. Specifically, data processor 15 constrains the vocabulary set to those words within a Bumex lexical tree. A user navigates menus during use of a clinical (e.g., ordering) application. Here the user is ordering Bumex, so user interface 26 displays appropriate choices within an ontology lexical tree, and constrains speech recognition to language entities that match it.

Figure 6:
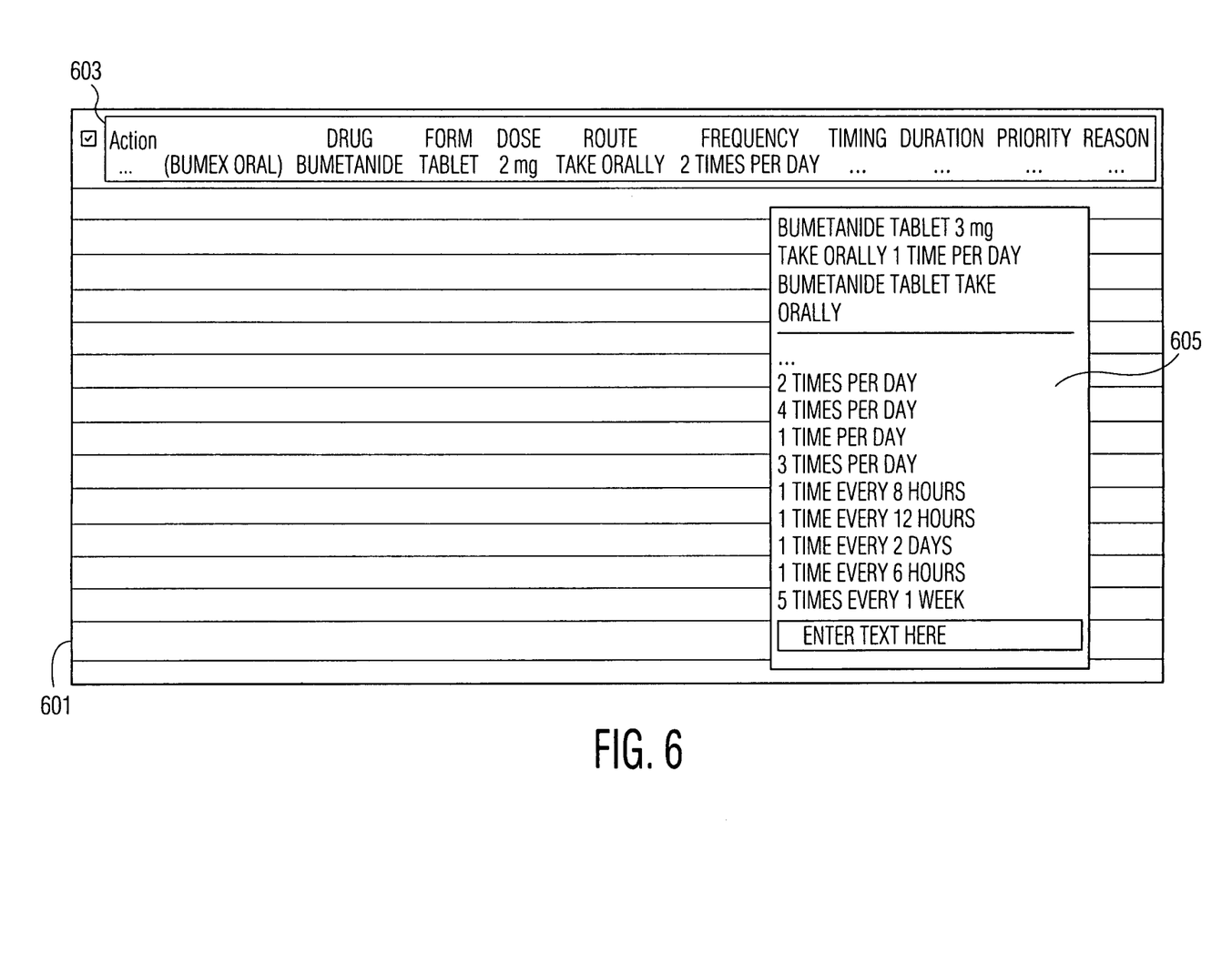
FIG. 6 illustrates an ordering menu initiated via the FIG. 5 menu, according to invention principles.

FIG. 6 illustrates ordering menu 601 initiated via the FIG. 5 menu in response to user voice commands. Data processor 15 selects an ontology from multiple different ontologies through the application, and through the relationships within the ontology. For example, ordering Bumex, selects the Order ontology, but also related ontologies, such as a local drug Formulary and Drug Information ontologies. Data processor 15 provides Bumex ordering information in row 603 of user interface image window 601 using local drug Formulary and Drug Information ontologies for presentation by user interface processor 26. Specifically, row 603 identifies a candidate Bumex order indicating, Drug name, form, dose, route of administration, frequency of administration and other data as needed. Window 605 presents a user with user selectable drug frequency of administration options.

Information repository 17 (FIG. 1) advantageously associates a speech recognition unit language model with a lexical tree word corpus of one or more ontologies. Information repository 17 maps recognized phonemes to recognized words. In another embodiment, alternate human interfaces, such as handwriting recognition interface may be used with, or instead of, speech recognition. A handwriting interface recognizes vector sequences (instead of phoneme phrases). The recognized vector sequences are mapped to characters, and the characters are mapped into words and words into phrases. The recognition uses an internal dictionary to identify plausible words, and relative probability of word phrases. In a similar manner to speech, a vocabulary is constrained by those matches which also fall within current ontologies, and within a current lexical branch of the ontology. The system is also used to structure spoken data into DICOM SR format for structured report preparation.

Figure 7:
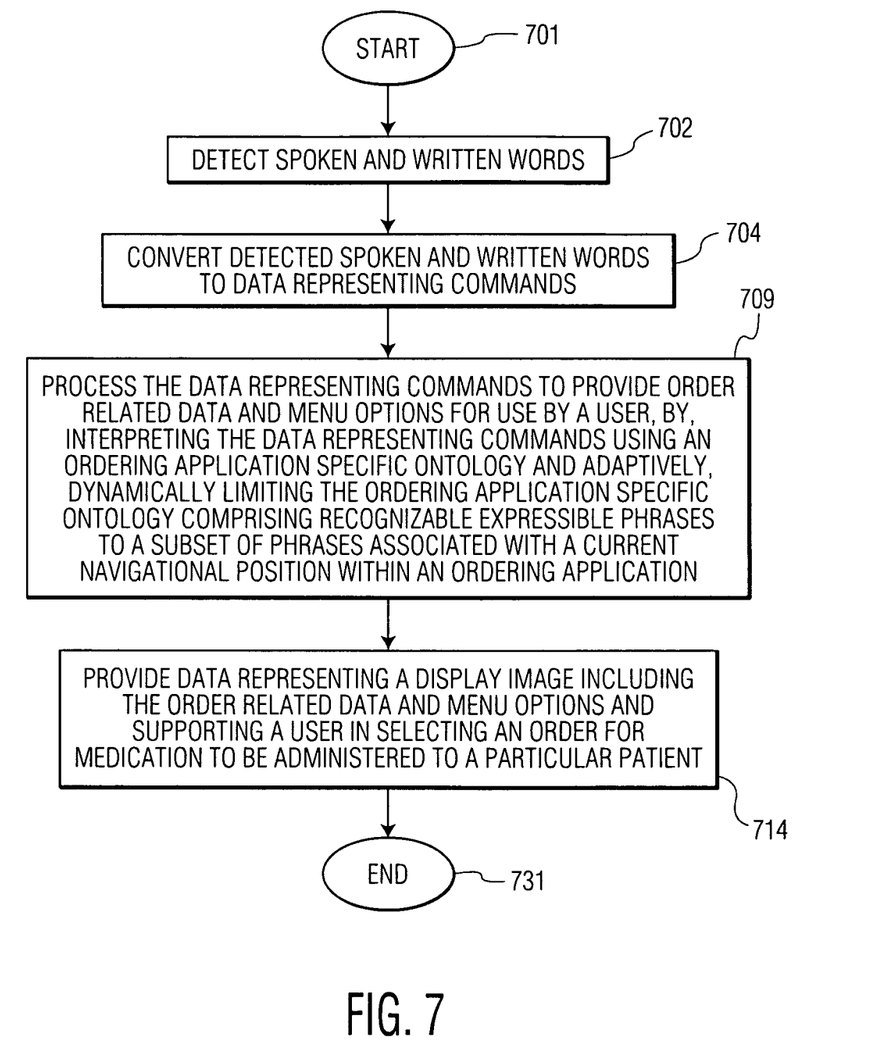
FIG. 7 shows a flowchart of a process used by a computerized integrated order entry and voice recognition system enabling voice responsive user entry of orders, according to invention principles.

FIG. 7 shows a flowchart of a process used by a computerized integrated order entry and voice recognition system enabling voice responsive user entry of orders. In step 702, following the start at step 701, voice recognition unit 19 (FIG. 1) including a handwriting recognition unit detects spoken and written words and in step 704 converts the detected spoken and written words to data representing commands. In step 709 data processor 15 processes the data representing commands to provide order related data and menu options for use by a user, by, interpreting the data representing commands using an ordering application specific ontology and excluding use of other non-ordering application specific ontologies. Data processor 15 adaptively, dynamically limits the ordering application specific ontology comprising recognizable expressible phrases to a subset of phrases associated with a current navigational position within an ordering application. Data processor 15 dynamically changes the subset of phrases in response to user navigation from one type of clinical treatment order to a different type of clinical treatment order. Data processor 15 dynamically initiates a search of the changed subset of phrases to identify a text phrase matching the data representing commands comprising a sequence of phonemes in response to user navigation from one type of clinical treatment order to a different type of clinical treatment order.

The ordering application specific ontology comprises an ordering application specific vocabulary including codes, terms and identifiers associated with particular orders and sets of orders and with particular medications and sets of medications and with laboratory tests, radiology tests, nursing services and observations, dietary and nutrition services, fluids, drains, dressings, procedures, treatments, infection control, physical and occupational therapy services, admission, discharge and transfer. The order related data comprises order related parameters identifying at least one of, (a) quantity, (b) a route of administration of a medical treatment, (c) a frequency of administering a treatment and (d) a form of medical treatment. The form of medical treatment comprises at least one of, (a) a package type, (b) a strength of a medical treatment and (c) a concentration of a medical treatment. The ordering application specific vocabulary comprises a drug formulary of a hospital and a drug information vocabulary.

The ordering application enables initiating an order for medication to be administered to a particular patient. In step 714, user interface processor 26 provides data representing a display image including the order related data and menu options provided by data processor 15, and supports a user in selecting an order for medication (including a treatment related service) to be administered to a particular patient. The process of FIG. 7 terminates at step 731.

Figure 8:
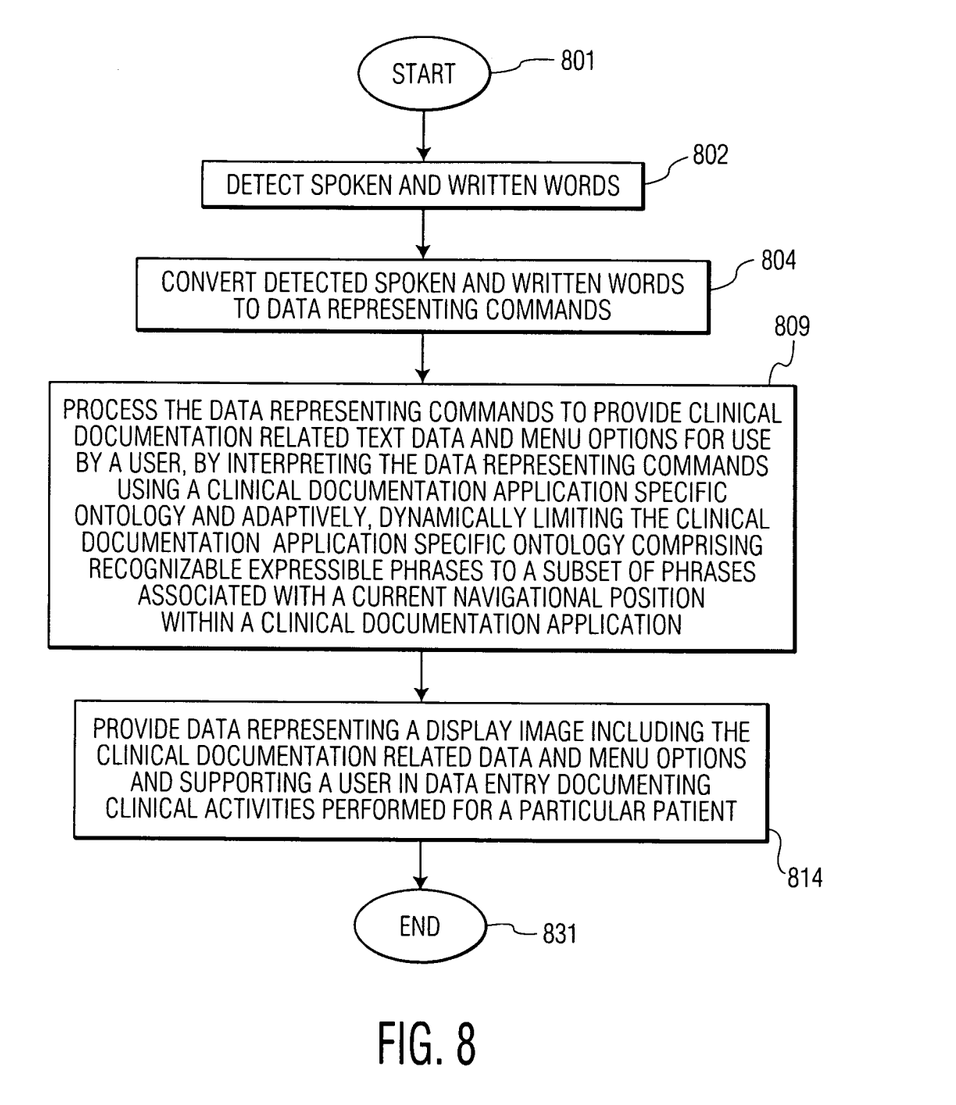
FIG. 8 shows a flowchart of a process used by a clinical documentation and voice recognition system enabling voice responsive clinical documentation, according to invention principles.

FIG. 8 shows a flowchart of a process used by a clinical documentation and voice recognition system enabling voice responsive clinical documentation. In step 802, following the start at step 801, voice recognition unit 19 (FIG. 1) including a handwriting recognition unit detects spoken and written words and in step 804 converts the detected spoken and written words to data representing commands. In step 809 data processor 15 processes the data representing commands to provide clinical documentation related text data and menu options for use by a user, by, interpreting the data representing commands using a clinical documentation application specific ontology and excluding use of other non-clinical documentation application specific ontologies. The clinical documentation application enables user data entry documenting clinical activities performed for a particular patient. Data processor 15 adaptively, dynamically limits the clinical documentation application specific ontology comprising recognizable expressible phrases to a subset of phrases associated with a current navigational position within a clinical documentation application. Data processor 15 dynamically changes the subset of phrases in response to user navigation from clinical documentation of data concerning a first anatomical organ to clinical documentation of a different second anatomical organ. Data processor 15 dynamically initiates a search of the changed subset of phrases to identify a text phrase matching the data representing commands comprising a sequence of phonemes in response to user navigation from clinical documentation of data concerning a first anatomical organ to clinical documentation of a different second anatomical organ.

Data processor 15 uses the data representing commands and multiple ontologies to determine what is to be documented, and when and where it is to be documented in clinical notes. Data processor 15 constrains interpretation of the data representing commands to terms and phrases concerning a current subject of documentation that are included in an ontology. Data processor 15 constrains interpretation of the data representing commands based on one or more of, (a) anatomy, (b) medical problem, (c) physiology, (d) pathophysiology, (e) best practices, (f) guidelines and (g) workflows. In step 714, user interface processor 26 provides data representing a display image including the clinical documentation related data and menu options provided by data processor 15 and supports a user in data entry documenting clinical activities performed for a particular patient. The process of FIG. 8 terminates at step 831.

The systems and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system advantageously associates a clinical ontology, used to represent decision-trees for knowledge-driven data entry of clinical information with constraints applied to automated recognition of speech and handwriting recognition. The processes and applications may, in alternative embodiments, be located on one or more (e.g., distributed) processing devices accessing a network linking the elements of FIG. 1. Further, any of the functions and steps provided in FIGS. 1-8 may be implemented in hardware, software or a combination of both and may reside on one or more processing devices located at any location of a network linking the elements of FIG. 1 or another linked network, including the Internet.

What is claimed is:

1. A computerized integrated order entry and voice recognition system enabling voice responsive user entry of orders, comprising:

a voice recognition unit for detecting spoken words and converting detected spoken words to data representing commands;

a data processor, coupled to said voice recognition unit, for processing said data representing commands provided by said voice recognition unit, to provide order related data and menu options for use by a user, by interpreting said data representing commands using an ordering application specific ontology and excluding use of other non-ordering application specific ontologies, and by,
   (a) constraining recognizable expressible phrases to a subset of said ordering application specific ontology in response to a current navigational position within said ordering application specific ontology and
   (b) constraining recognizable expressible phrases to phrases in a lexical hierarchy associated with said subset, in response to a current navigational position within said lexical hierarchy, said ordering application enabling initiating an order for medication to be administered to a particular patient; and a user interface processor, coupled to said data processor, for providing data representing a display image, said display image,
   including said order related data and menu options provided by said data processor and
   supporting a user in selecting an order for medication to be administered to a particular patient.

2. A system according to claim 1, wherein
said data processor adaptively, dynamically limits said expressible phrases to words within said lexical hierarchy associated with said subset and
probabilistically matches said words to detected phonemes.

3. A system according to claim 2, wherein
said data processor dynamically changes said subset of phrases in response to user navigation from one type of clinical treatment order to a different type of clinical treatment order.

4. A system according to claim 3, wherein
said data processor dynamically initiates a search of the changed subset of phrases to identify a text phrase matching said data representing commands comprising a sequence of phonemes in response to user navigation from one type of clinical treatment order to a different type of clinical treatment order.

5. A system according to claim 1, wherein
said ordering application specific ontology comprises an ordering application specific vocabulary.

6. A system according to claim 5, wherein
said ordering application specific vocabulary comprises codes, terms and identifiers associated with particular orders and sets of orders.

7. A system according to claim 5, wherein
said order related data comprises order related parameters identifying at least one of, (a) quantity, (b) a route of administration of a medical treatment, (c) a frequency of administering a treatment and (d) a form of medical treatment.

8. A system according to claim 7, wherein
said form of medical treatment comprises at least one of, (a) a package type, (b) a strength of a medical treatment and (c) a concentration of a medical treatment.

9. A system according to claim 5, wherein
said ordering application specific vocabulary comprises a drug formulary of a hospital.

10. A system according to claim 9, wherein
said ordering application specific vocabulary comprises a drug information vocabulary.

11. A system according to claim 5, wherein
said ordering application specific vocabulary comprises codes, terms and identifiers associated with particular medications and sets of medications and with laboratory tests, radiology tests, nursing services and observations, dietary and nutrition services, fluids, drains, dressings, procedures, treatments, infection control, physical and occupational therapy services, admission, discharge and transfer.

12. A system according to claim 1, wherein
said medication also includes a treatment related service.

13. A system according to claim 1, including
a handwriting recognition unit for converting detected written words to data representing commands.

14. A system according to claim 13, wherein
said handwriting recognition unit converts detected written words of orders and clinical documentation to data representing commands.

15. A computerized clinical documentation and voice recognition system enabling voice responsive user completion of clinical documentation, comprising:
a voice recognition unit for detecting spoken words and converting detected spoken words to data representing commands;
a data processor, coupled to said voice recognition unit, for processing said data representing commands provided by said voice recognition unit, to provide clinical documentation related text data and menu options for use by a user, by interpreting said data representing commands using a clinical documentation application specific ontology and excluding use of other non-clinical documentation application specific ontologies, and by,
(a) constraining recognizable expressible phrases to a subset of said clinical documentation application specific ontology in response to a current navigational position within said clinical documentation application specific ontology and
(b) constraining recognizable expressible phrases to phrases in a lexical hierarchy associated with said subset, in response to a current navigational position within said lexical hierarchy, said clinical documentation application enabling user data entry documenting clinical activities performed for a particular patient; and
a user interface processor, coupled to said data processor, for providing data representing a display image, said display image,
including said clinical documentation related data and menu options provided by said data processor and
supporting a user in data entry documenting clinical activities performed for a particular patient.

16. A system according to claim 15, wherein
said data processor adaptively, dynamically limits said expressible phrases to words within said lexical hierarchy associated with said subset and
probabilistically matches said words to detected phonemes.

17. A system according to claim 16, wherein
said data processor dynamically changes said subset of phrases in response to user navigation from clinical documentation of data concerning a first anatomical organ to clinical documentation of a different second anatomical organ.

18. A system according to claim 17, wherein
said data processor dynamically initiates a search of the changed subset of phrases to identify a text phrase matching a sequence of phonemes in response to user navigation from clinical documentation of data concerning a first anatomical organ to clinical documentation of a different second anatomical organ.

19. A system according to claim 15, wherein
said data processor uses said data representing commands and a plurality of ontologies to determine what is to be documented, and when and where it is to be documented in clinical notes.

20. A system according to claim 19, wherein
said data processor constrains interpretation of said data representing commands to terms and phrases concerning a current subject of documentation included in an ontology.

21. A system according to claim 19, wherein
said data processor constrains interpretation of said data representing commands based on at least two of, (a) anatomy, (b) medical problem, (c) physiology, (d) pathophysiology, (e) best practices, (f) guidelines and (g) workflows.

22. A method employed by a computerized integrated order entry and voice recognition system enabling voice responsive user entry of orders, comprising the activities of:
detecting spoken words;
converting the detected spoken words to data representing commands;
processing said data representing commands to provide order related data and menu options for use by a user, by, interpreting said data representing commands using an ordering application specific ontology and excluding use of other non-ordering application specific ontologies, said ordering application enabling initiating an order for medication to be administered to a particular patient, adaptively, dynamically limiting said ordering application specific ontology comprising recognizable expressible phrases to a subset of phrases associated with a current navigational position within an ordering application and limiting recognizable expressible phrases to phrases in a lexical hierarchy associated with said subset, in response to a current navigational position within said lexical hierarchy; and providing data representing a display image, said display image, including said order related data and menu options provided by said data processor and supporting a user in selecting an order for medication to be administered to a particular patient.

* * * * *